(12) United States Patent
Malin

(10) Patent No.: US 7,044,735 B2
(45) Date of Patent: May 16, 2006

(54) METHOD OF INSTALLING A DENTAL IMPLANT

(75) Inventor: Leo J. Malin, N3622 Brookview Rd., La Crosse, WI (US) 54601

(73) Assignee: Leo J. Malin, La Crosse, WI (US)

( * ) Notice: Subject to any disclaimer, the term of this patent is extended or adjusted under 35 U.S.C. 154(b) by 459 days.

(21) Appl. No.: 10/429,088

(22) Filed: May 2, 2003

(65) Prior Publication Data

US 2004/0219480 A1 Nov. 4, 2004

(51) Int. Cl.
*A61C 3/00* (2006.01)
(52) U.S. Cl. .................................... 433/75; 433/215
(58) Field of Classification Search ................ 433/75, 433/72, 215, 74, 173, 174
See application file for complete search history.

(56) References Cited

U.S. PATENT DOCUMENTS

| 3,748,739 A | 7/1973 | Thibert |
| 4,998,881 A | 3/1991 | Lauks |
| 5,015,183 A | 5/1991 | Fenick |
| 5,015,186 A | 5/1991 | Detsch |
| 5,064,374 A | 11/1991 | Lundgren |
| 5,133,660 A | 7/1992 | Fenick |
| 5,350,297 A | 9/1994 | Cohen |
| 5,415,546 A * | 5/1995 | Cox, Sr. ..................... 433/213 |
| 5,613,852 A | 3/1997 | Bavitz |
| 5,718,579 A | 2/1998 | Kennedy |
| 5,725,376 A * | 3/1998 | Poirier ....................... 433/172 |
| 5,967,777 A * | 10/1999 | Klein et al. ................... 433/75 |
| 6,283,753 B1 | 9/2001 | Willoughby |
| 6,319,006 B1 * | 11/2001 | Scherer et al. .............. 433/215 |
| RE37,646 E | 4/2002 | Zuest |
| 6,488,502 B1 | 12/2002 | Weber |
| 2002/0182567 A1 | 12/2002 | Hurson et al. |

FOREIGN PATENT DOCUMENTS

| EP | 0437031 A1 | 7/1991 |
| WO | WO99/26540 | 6/1999 |

* cited by examiner

*Primary Examiner*—Melba N. Bumgarner
(74) *Attorney, Agent, or Firm*—Robert J. Harter

(57) ABSTRACT

A method of installing a dental implant includes positioning a drill guide tube adjacent to a jawbone and taking a tomographical scan of the two. Based on the scan, a computer-generated image is created and analyzed to confirm whether the drill guide tube is properly aligned. If the drill guide tube is in the correct position, that same tube to used to guide a drill bit into the jawbone. In some cases, the tube also helps guide a biopsy punch in cutting just a small, round opening into the gum tissue, which minimizes the time needed for healing.

6 Claims, 6 Drawing Sheets

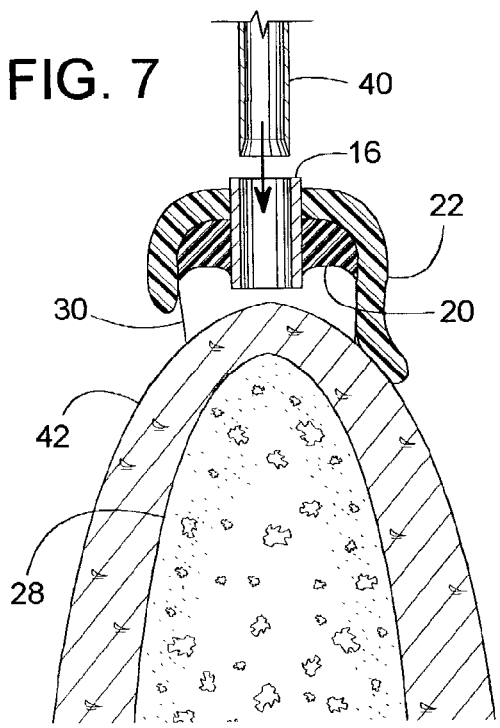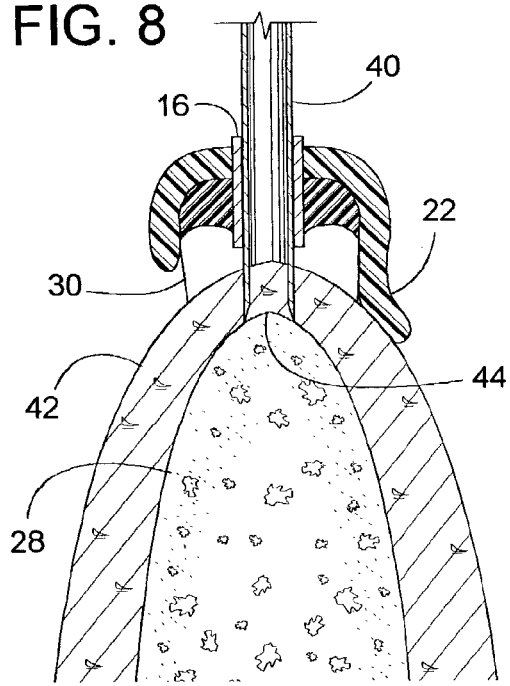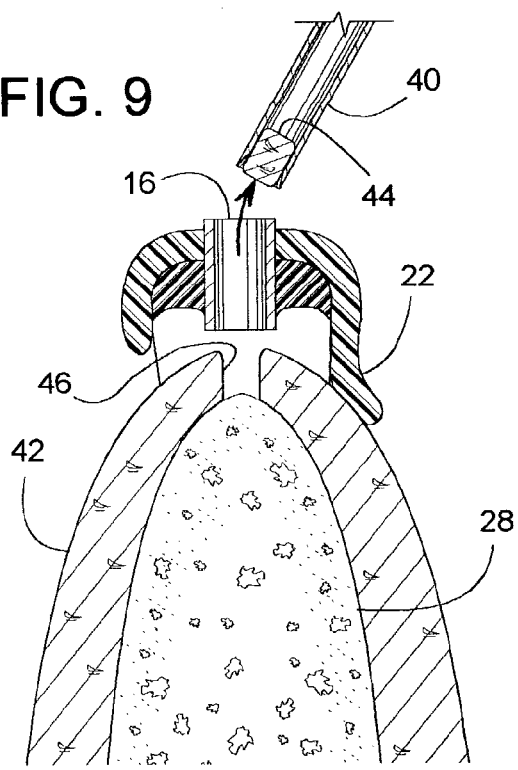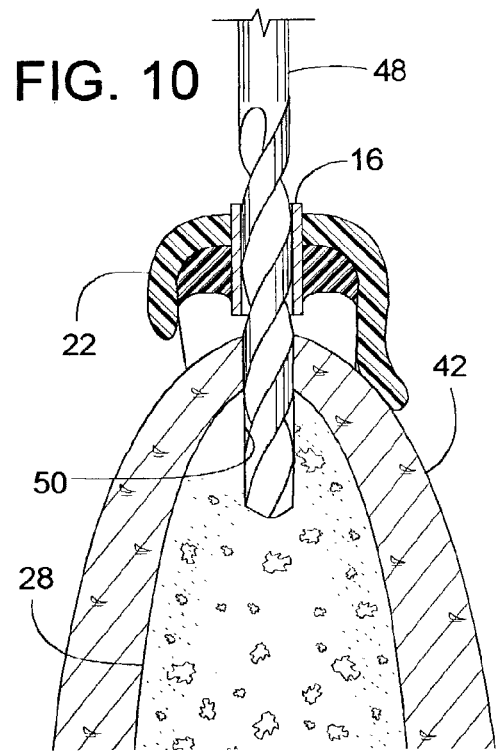

METHOD OF INSTALLING A DENTAL IMPLANT

BACKGROUND OF THE INVENTION

1. Field of the Invention

The subject invention generally pertains to dental implants and more specifically to a method of installing them.

2. Description of Related Art

Various dental implant methods and devices have been developed for replacing one or more missing teeth in a person's jaw with prosthetic teeth. For many prosthetic teeth, a final product comprises three basic components: an implant, an abutment, and a crown. The crown is the exposed portion of the prosthesis that resembles one or more teeth. The implant is an anchor that becomes attached to the jawbone, and the abutment couples the crown to the implant.

Typical implant methods involve a series of procedures extending over several months. In some cases, for instance, the process involves first, cutting the gum tissue in the area of the missing tooth and pulling the tissue back to expose the jawbone; second, drilling a hole into the bone; third, installing an anchoring member or implant into the hole; fourth, attaching a cover screw to the implant and stitching the gum tissue back together; fifth, waiting up to several months to allow the gum tissue to heal over the cover screw and to allow the bone to grow onto the implant; sixth, cutting a small round hole in the gum tissue to remove the cover screw and expose the implant; seventh, attaching a healing cap to the implant; waiting another extended period to allow the gum tissue to heal around the healing cap; eighth, replacing the healing cap with an abutment; and ninth, attaching a crown (e.g., an individual prosthetic tooth, bridge, denture, etc.) to the abutment.

An implant process can be improved with the aid of drill guide bushings and tomography as disclosed in PCT Publication WO 99/26540 by Klein et al. (specifically incorporated by reference herein). The Klein method involves taking a CT scan (computed tomography scan) of a patient wearing a surgical template that overlays the patient's teeth. The surgical template preferably has three fiducial markers that are detected by the CT scan. After taking the tomographical scan, the surgical template is removed from the patient's mouth and placed over a model of the patient's jaw. The model jaw with the surgical template is loaded onto a computer-driven milling machine. With the aid of the CT scan data and the three fiducial markers, the milling machine accurately drills a hole into the surgical template. The template, now with an accurately drilled hole, is returned to the patient's mouth, so the hole in the template can then be used as a drill guide when drilling into the patient's actual jawbone. Drawbacks of such a method include its overall complexity and the expense of the computer-driven milling machine.

Another implant method and related device is disclosed by Fenick in U.S. Pat. Nos. 5,015,183 and 5,133,660, which are specifically incorporated by reference herein. Fenick uses X-rays to help identify a drill bit trajectory and uses drill guide bushings to help guide the drill bit. The Fenick system creates a radiology stent that includes a radially opaque grid. The stent, without any drill bushings, is X-rayed while in the patient's mouth. The stent is then placed over a model of the patient's jaw where the grid provides a frame of reference that helps in manually positioning a drill bit relative to the model jaw. A hole is drilled into the model, and the resulting hole helps align a drill bushing relative to the model. Next, a cast is created over the model to capture the drill bushing. The cast, with the drill bushing, is then placed in the patient's mouth to help guide the drill bit that drills a hole into the patient's jawbone. With the Fenick system, some positional accuracy may be sacrificed because the drill bushing is aligned to a model rather than being aligned directly to the patient's actual jaw.

Various other examples of dental implant methods and devices are disclosed in U.S. Pat. Nos. 6,283,753; 5,718,579; 5,613,852; 5,064,374; 5,015,186; RE37,646; 3,748,739; 5,350,297; 6,488,502; 4,998,881; all of which are specifically incorporated by reference herein. Additional examples of dental implant methods and devices are disclosed in U.S. Patent Application Publication US 2002/0182567 and European Patent Application 0437031A1; both of which are specifically incorporated by reference herein.

SUMMARY OF THE INVENTION

To provide a better method of installing a dental implant, it is an object of some embodiments of the invention to take a tomographical scan of a drill guide tube adjacent to a jawbone and to use that same tube for guiding a drill bit into the jawbone.

In some embodiments, the implant placement direction and angulation are determined by first establishing the occlusal scheme of the proposed final restoration. The process ensures that the implant placement will properly align the implant to the center of the final occlusal table. The occlusal forces then applied to that implant will be in as a direct line as possible, thereby reducing off-axis inappropriate loading final occlusion dictated placement and angulation of the implant.

Another object of some embodiments is to minimize the cutting of gum tissue in the area where a dental implant is to be installed.

Another object of some embodiments is to reposition a drill guide tube by referring to a computer-generated image created from a tomographical scan of the tube's original position relative to a jawbone.

Another object of some embodiments is to reposition a drill guide tube by rotation, wherein the center of rotation is near the occlusal plane rather than near the gum line.

Another object of some embodiments is to take a second tomographical scan of the tube and the jawbone to confirm that the tube is properly aligned after the tube is repositioned.

Another object of some embodiment is to accurately position a circular cutter so that, prior to drilling into the bone, a relatively small, round hole can be cut into the gum tissue rather making a more evasive cut and pulling back the tissue to expose the bone for drilling.

Another object of some embodiments is to use a tube to guide a circular cutter as the cutter cuts a generally round opening into the gum tissue.

Another object of some embodiments is to cut a generally round opening into the gum tissue using a biopsy punch, whereby the biopsy punch can be further used to remove a round plug of tissue after the round opening has been cut.

Another object of some embodiments is to use a model jaw for creating a stent that can hold a guide tube adjacent to a jawbone while a tomographical scan is taken of the tube and the jawbone.

Another object of some embodiments is to cement a drill guide tube to a stent prior to a tomographical scan indicating that the tube is properly aligned.

Another object of some embodiments is to cement a drill guide tube to a stent after a tomographical scan indicates that the tube is improperly aligned.

Another object of some embodiments is to enlarge a hole in a jawbone by first removing a stent that holds a guide tube adjacent to the jawbone.

Another object of some embodiments is to skip the use of a cover screw by cutting a properly sized round opening in the gum tissue, drilling a hole into the jawbone, inserting an implant into the hole, and installing a healing cap instead of a cover screw, whereby the healing cap prevents the tissue from completely healing over the opening.

One or more of these and other objects of the invention are provided by positioning a drill guide tube adjacent to a jawbone, taking a tomographical scan of the tube and the jawbone simultaneously, analyzing a computer-generated image that is based on the tomographical scan, repositioning the tube if necessary, and using the tube to guide a drill bit into the jawbone.

BRIEF DESCRIPTION OF THE DRAWING

FIG. 7 is a cross-sectional view taken along a longitudinal centerline of a drill guide tube, wherein the drawing illustrates the step of inserting a circular cutter through the drill guide tube.

FIG. 8 is a cross-sectional view similar to FIG. 7 but showing the step of cutting a substantially round opening in the gum tissue that overlays a jawbone.

FIG. 9 is a cross-sectional view similar to FIG. 7 but showing a circular cutter being withdrawn from the tube, thereby leaving a substantially round hole in the gum tissue.

FIG. 10 is a cross-sectional view similar to FIG. 7 but showing a drill bit drilling a hole into the jawbone.

DESCRIPTION OF THE PREFERRED EMBODIMENT

For simplicity and clarity, the invention will be described with reference to replacing a single missing tooth, however, it will be appreciated by those skilled in the art that the method can be readily applied to multiple teeth or even an entire set of teeth. Thus, the term, "crown" broadly encompasses an individual prosthetic tooth, bridge, denture, etc. For the illustrated example, a patient 10 is missing his lower-right cuspid as shown in FIGS. 1–4.

To replace the missing tooth, the process may begin by creating a cast model 12 (FIG. 1) of the patient's lower jaw. Arrow 14 indicates the general area of the missing tooth. Model 12 may be a plaster casting; however, the actual structure and method of making such a model may vary. Such models and methods of making them are well known to those skilled in the art.

Figure 1:
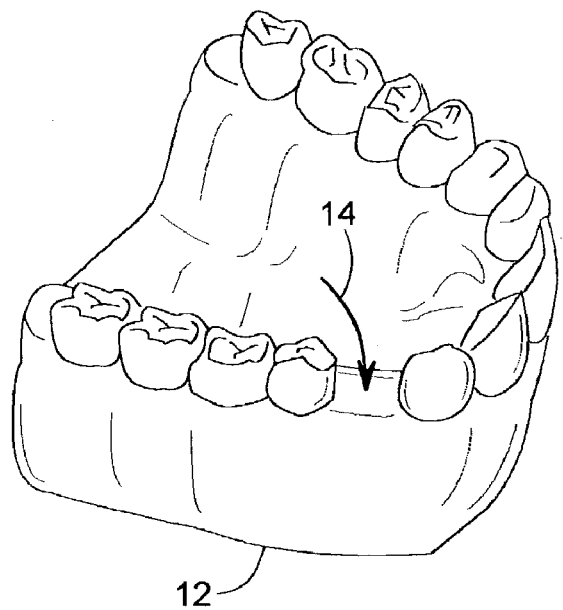
FIG. 1 is a perspective view illustrating the step of creating a model jaw, wherein the jaw shows the area of at least one missing tooth.
Figure 2:
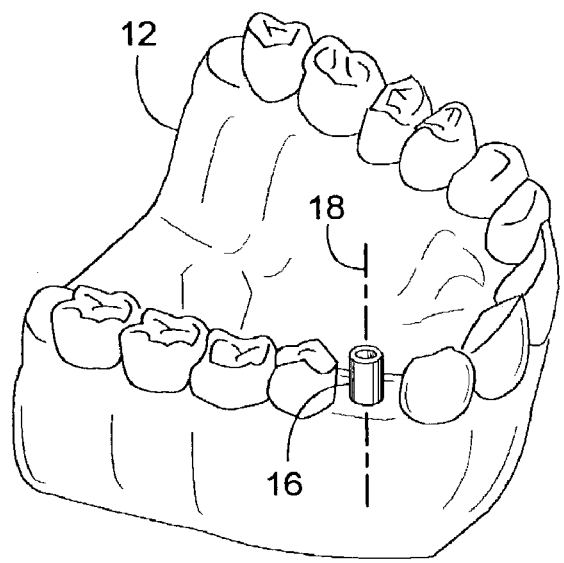
FIG. 2 is a perspective view of the model of FIG. 1, but the drawing also shows a drill guide tube in the area of the missing tooth.

In FIG. 2, a drill guide tube 16, can be placed on model 12 in the area of the missing tooth. Tube 16 is preferably made of metal or some other generally radially opaque material. The tube's longitudinal centerline 18 should lie generally along the anticipated centerline of the prosthetic tooth and its supporting implant. In some cases, tube 16 is preferably held temporarily to model 12 using some type of clamp or bonding material. Examples of such a clamp include, but are not limited to, a fastener, screw, nail, tack, etc., and examples of a bonding material (see material 20 of FIG. 7) include, but are not limited to wax, adhesive, thermoplastic, etc. In other embodiments of the invention, tube 16 is placed in the area of the missing tooth after a stent is made.

Figure 3:
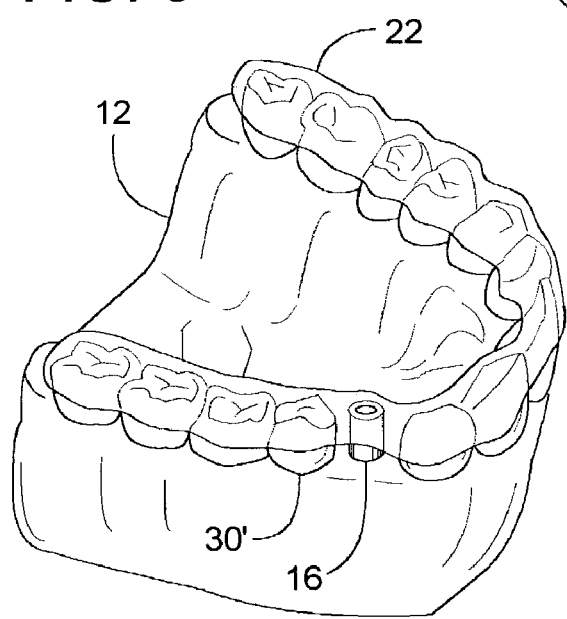
FIG. 3 is a perspective view illustrating the step of creating a stent that overlays the model jaw.

In FIG. 3, a surgical stent 22 is made by vacuum-forming an acrylic sheet over model 12; however, it should be appreciated by those skilled in the art that there are other ways of making a surgical stent that are well within the scope of the invention. In some embodiments of the invention, stent 22 is formed over both model 12 and tube 16. Once stent 22 is formed, a small hole in the stent can be drilled or cut away so that the stent does not close off the inner bore of tube 16. In some cases, tube 16 may be repositioned to protrude through the hole. In some embodiments, stent 22 is formed over model 12 without tube 16 in place, and tube 16 is attached to stent 22 afterwards. In the later case, a temporary removable filler member or plug (e.g., cylindrical or tooth shaped) may need to be installed on model 12 in the area of the missing tooth to reserve space for tube 16 within stent 22. After stent 22 is made, tube 16 can be affixed to the stent in the space left by the filler member. Again, a small hole can be cut away or drilled through stent 22 to open the inner bore of tube 16.

Figure 4:
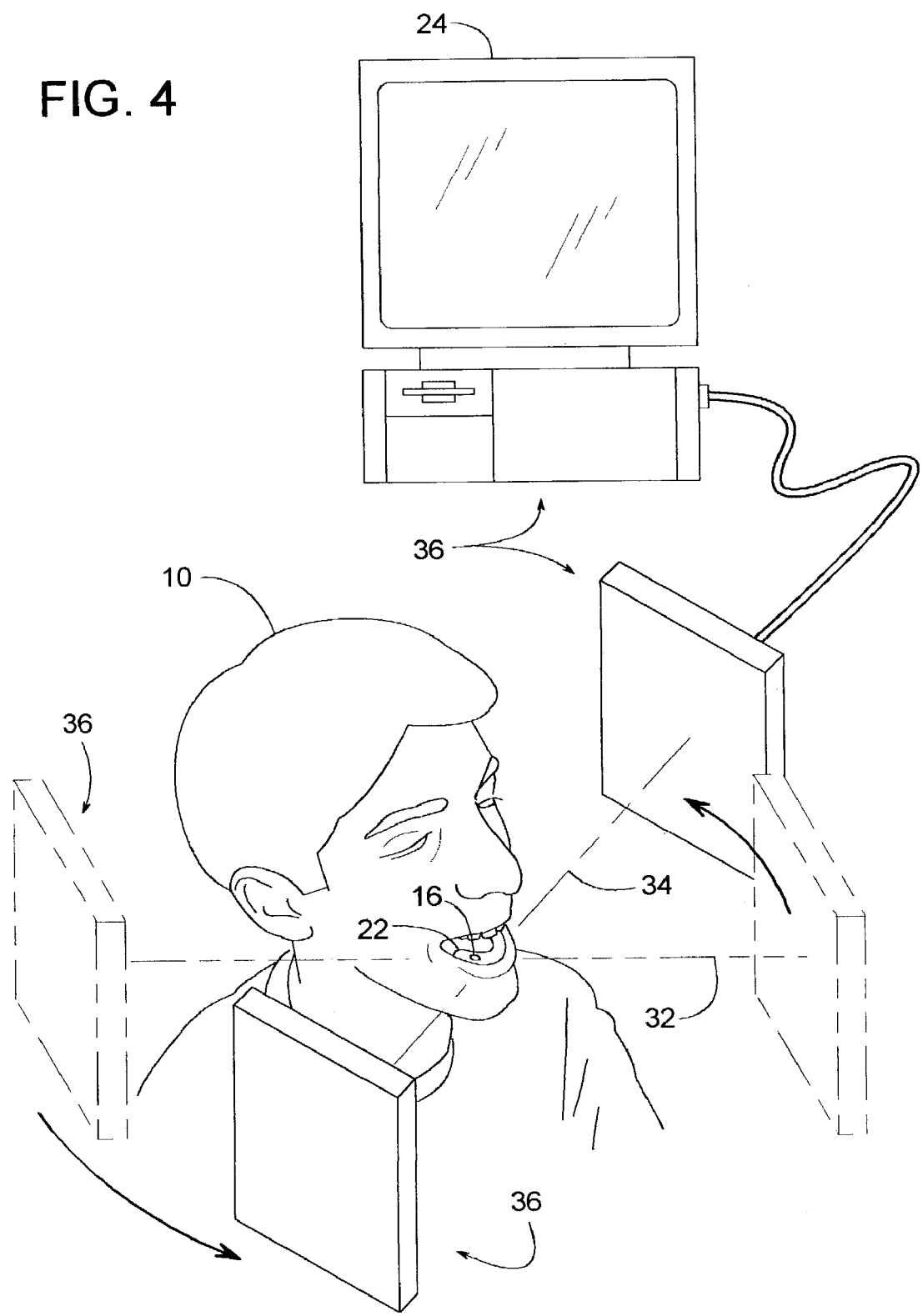
FIG. 4 is a perspective view illustrating the step of taking a tomographical scan of a tube in relation to a bone and creating a plurality of images therefrom.
Figure 5:
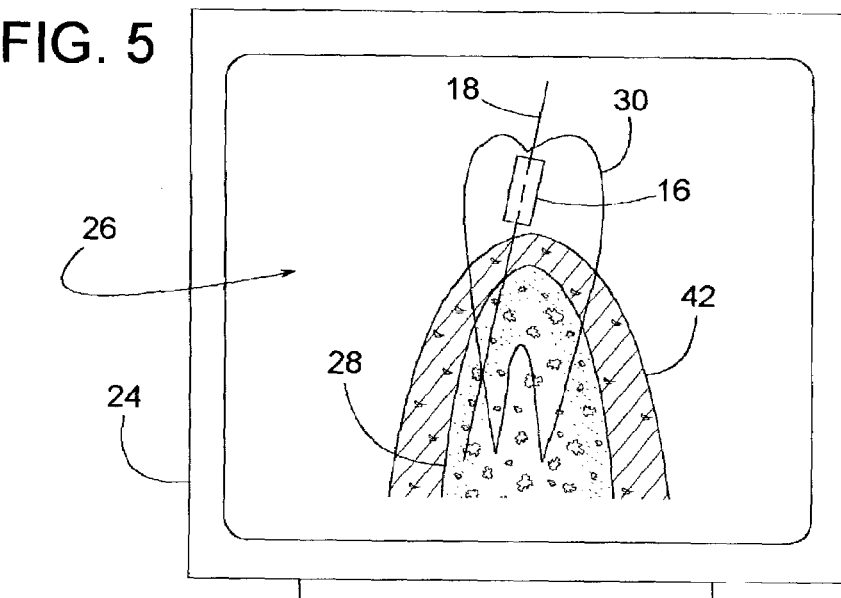
FIG. 5 illustrates the step of creating a first image of a tube at a first position relative to a bone.

Regardless of how the stent is made, stent 22 with the attached tube 16 is placed on the patient's lower jaw as shown in FIG. 4. This places tube 16 in the actual area of the missing tooth with the tube being in the same relative orientation as it was when the stent and tube were on model 12. A tomographical scan is taken of the patient's jaw to record the position of tube 16 relative to a bone 28 (i.e., the patient's upper or lower jawbone). For illustrative purposes, the patient's mouth is shown open only to show that stent 22 and tube 16 are in the patient's mouth. From the tomographical scan, a computer 24 creates a first image 26 that shows tube 16 at a first position in relation to bone 28 as shown in FIG. 5. For reference purposes only, an outline of an adjacent tooth 30 is also shown in image 26, wherein tooth 30 corresponds to a lower-right first bicuspid 30' of the model in FIG. 1.

The equipment and method for taking a tomographical scan is well known to those skilled in the art. Tomography generally involves creating a computer-generated image (e.g., image 26) from a plurality of X-rays as indicated by lines 32 and 34 of FIG. 4. Other terms used for tomography include, but are not limited to, CT scan (computed tomographical scan), EIT (electrical impedance tomography), CAT scan (computerized axial tomography). System 36 of FIG. 4 is schematically illustrated to represent all types tomography systems. Some examples of system 36 include, but are not limited to a CommCAT IS-2000, Panorex CMT, and a Panorex CMT Plus, all of which are products of Imaging Sciences International, Inc., of Hatfield, Pa.

Figure 6:
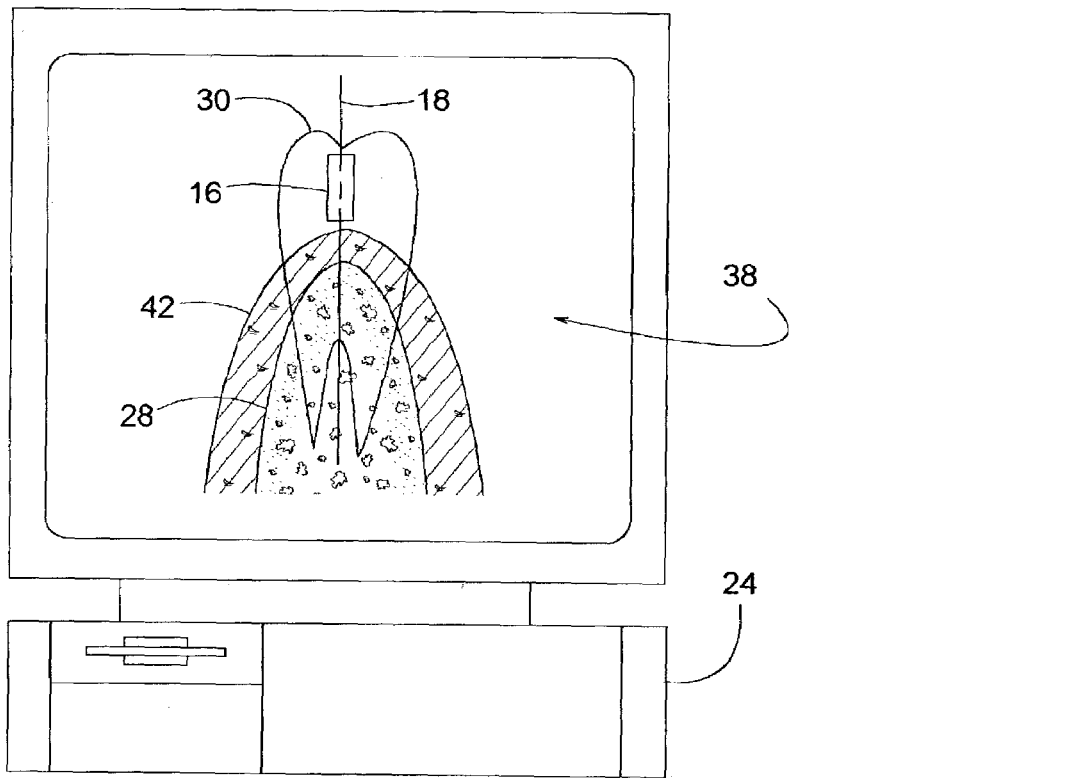
FIG. 6 illustrates the step of creating a second image of a tube at a second position relative to a bone.

Image 26 of FIG. 5 shows that drill guide tube 16 is not properly aimed toward bone 28, so in this particular case, the next step in the process would be to reposition tube 16. A second image 38 of FIG. 6 illustrates the step of repositioning tube 16 to a second position. Repositioning tube 16 simply involves releasing the clamp or bonding material that holds tube 16 to sent 22, and reaffixing the tube at the second position shown in FIG. 6. Once tube 16 is fixed at the second position, system 36 takes another tomographical scan of the patient with stent 22 and tube 16 again in the patient's mouth. The resulting second image of FIG. 6 shows that tube 16 is now properly aligned relative to bone 28, so tube 16 can now be used as a tool guide.

In FIG. 7, a circular cutter 40 is inserted through tube 16. Circular cutter 40 represents any cutter that can cut a substantially round opening into gum tissue 42 that covers bone 28. One example of cutter 40 is a cylindrical biopsy punch.

In FIG. 8, cutter 40 is shown cutting a substantially round opening into gum tissue 42, while tube 16 helps guide the angular position of cutter 40 relative to bone 28. To help hold tube 16 at its proper position, it should be noted that stent 22 engages the patient's teeth (e.g., tooth 30) and/or the patient's gums 42 (in the case where a patient has no teeth).

In FIG. 9, cutter 40 is shown withdrawing a round plug 44 of gum tissue as cutter 40 is withdrawn from tube 16. This leaves a substantially round opening 46 in gum tissue 42.

In FIG. 10, a drill bit 48 is inserted through tube 16, so tube 16 can help guide the drill bit as the drill bit drills a hole 50 into bone 28.

Figure 11:
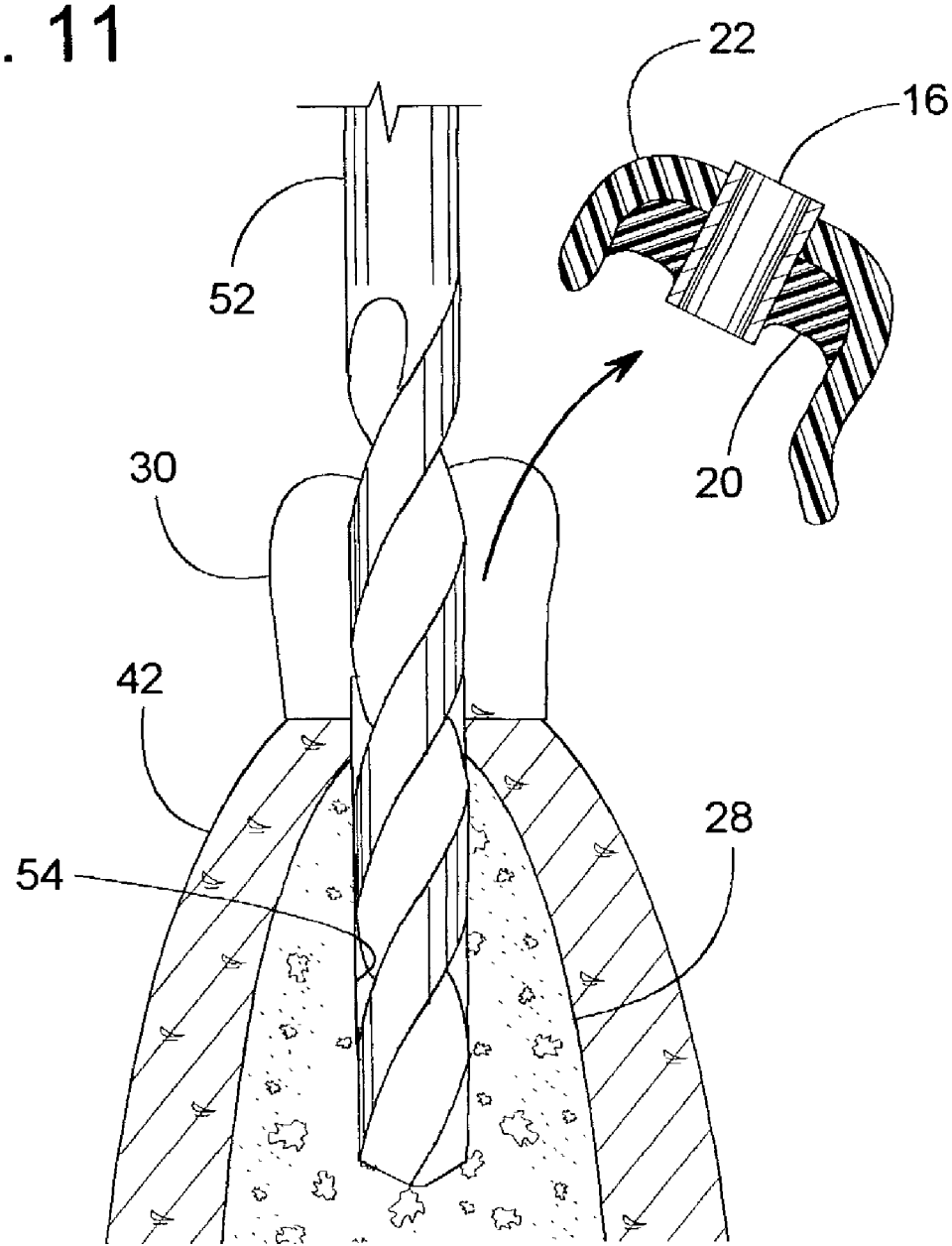
FIG. 11 is a cross-sectional view similar to FIG. 7 but showing the stent being removed and the hole in the jawbone being enlarged.

In FIG. 11, stent 22 and tube 16 are entirely removed from the patient's mouth to allow room for a larger drill bit 52 to enlarge hole 50 in diameter and/or depth, thereby producing an enlarged hole 54.

Figure 12:
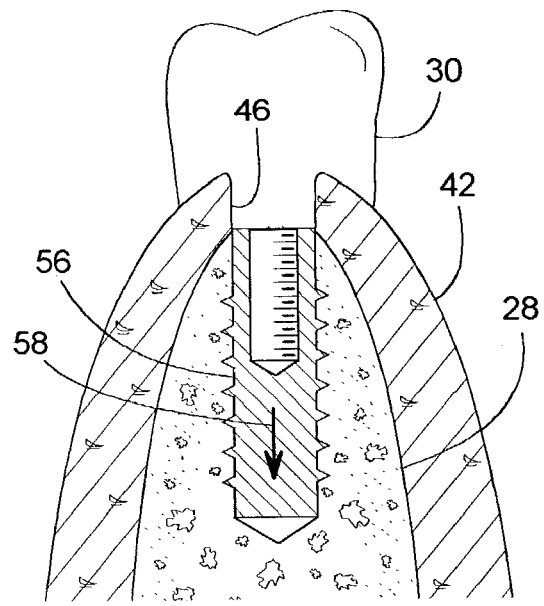
FIG. 12 is a cross-sectional view similar to FIG. 7 but showing an implant being inserted into a hole that was drilled into the jawbone.

In FIG. 12, a conventional implant 56 is shown being inserted (arrow 58) and anchored into hole 50 (enlarged to hole 54). The actual structure of implant 56 may vary widely as can be appreciated by those skilled in the art.

Figure 13:
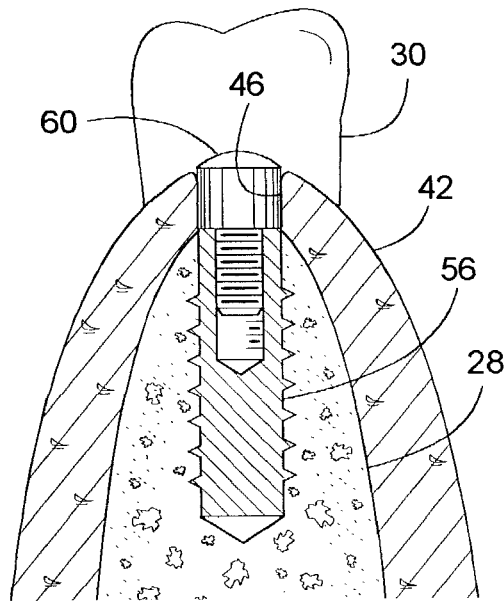
FIG. 13 is a cross-sectional view similar to FIG. 7 but showing a healing cap being attached to the implant.

In FIG. 13, a healing cap 60 is attached to implant 56 to allow the gum tissue 42 to heal around the perimeter of opening 46. Healing cap 60 protrudes sufficiently above gum tissue 42 to inhibit tissue 42 from completely closing opening 46 at any time during a period extending from when opening 46 was first created (FIG. 9) until healing cap 60 is removed from implant 56 (FIG. 14).

Figure 14:
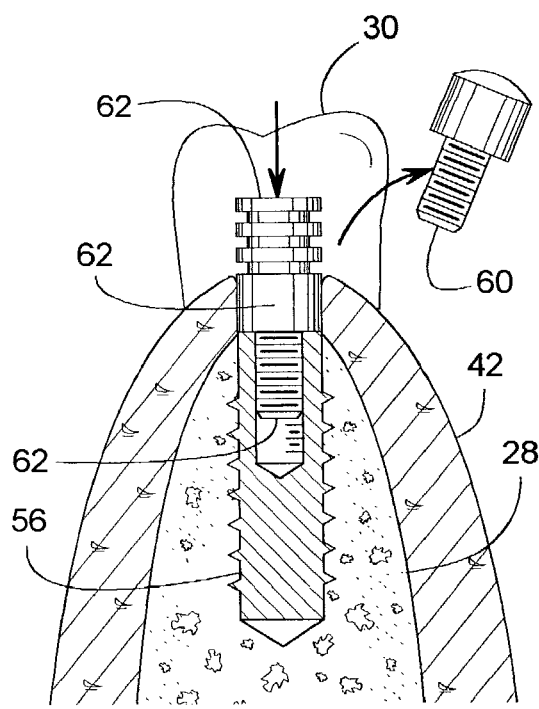
FIG. 14 is a cross-sectional view similar to FIG. 7 but showing the abutment replacing the healing cap.
Figure 15:
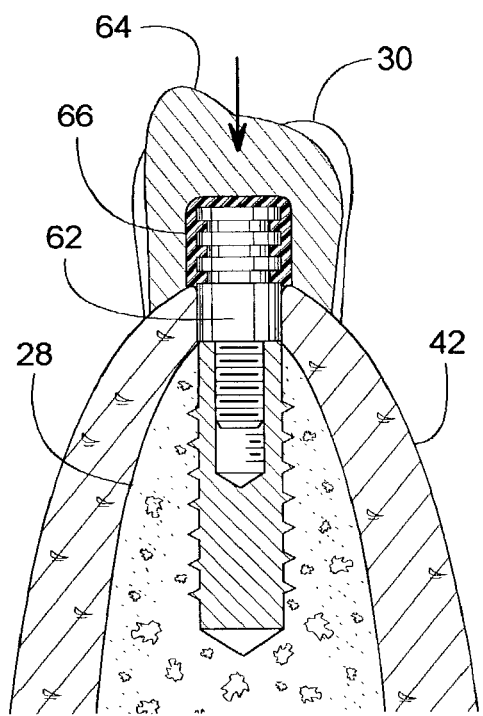
FIG. 15 is a cross-sectional view similar to FIG. 7 but showing a crown or similar item being attached to the abutment.

In FIG. 14, healing cap 60 is removed from implant 56, and a conventional abutment 62 is attached to implant 56. The actual structure of abutment 62 may vary widely as can be appreciated by those skilled in the art In FIG. 15, a crown 64 (e.g., an individual prosthetic tooth, bridge, denture, etc.) is attached to abutment 62. Crown 64 can be bonded and/or mechanically fastened to abutment 62. In some cases, for example, a bonding material 66 bonds crown 64 to abutment 62.

Although the invention is described with reference to a preferred embodiment, it should be appreciated by those skilled in the art that various modifications are well within the scope of the invention. Therefore, the scope of the invention is to be determined by reference to the claims that follow.

I claim:

1. A method of installing a dental implant in a bone that is adjacent to gum tissue, wherein the bone is part of at least one of an upper jaw and a lower jaw of a patient, the method comprising:
    creating a model of at least one of the upper jaw and the lower jaw;
    creating a stent that overlays the model;
    holding a tube at a first position within the stent;
    placing the stent and the tube adjacent to at least one of the lower jaw and the upper jaw of a patient;
    creating a first image that shows the first position of the tube relative to the bone;
    viewing the first image;
    in response to viewing the first image, repositioning the tube to a second position in relation to the stent;
    after repositioning the tube to the second position, creating a second image that shows the second position of the tube relative to the bone;
    cementing the tube to the stent at the second position;
    cutting the gum tissue with a circular cutter to create a substantially round opening in the gum tissue;
    inserting a drill bit through the tube, whereby the tube helps guide the drill bit;
    drilling a hole into the bone;
    inserting the dental implant into the hole;
    attaching a healing cap to the dental implant to allow the gum tissue to heal around the healing cap;
    allowing the gum tissue to heal around the healing cap;
    inhibiting the gum tissue from completely closing the opening at any time during a period extending from when the substantially round opening was first created until the healing cap is removed from the dental implant;
    removing the healing cap from the dental implant while avoiding any further appreciable cutting of the gum tissue;
    attaching an abutment to the dental implant; and
    attaching a crown to the abutment.

2. The method of claim 1, wherein the first image and the second image are derived from tomographical scans of the tube and the bone.

3. The method of claim 1, further comprising inserting the circular cutter through the tube so the tube can help guide the circular cutter as the circular cutter cuts the substantially round opening.

4. The method of claim 1, wherein the circular cutter is a cylindrical biopsy punch.

5. The method of claim 1, further comprising:
    moving the stent away from the bone after the step of drilling the hole into the bone; and
    increasing a depth of the hole after moving the stent away from the bone.

6. The method of claim 1, further comprising:
    moving the stent away from the bone after the step of drilling the hole into the bone; and
    increasing a diameter of the hole after moving the stent away from the bone.

* * * * *